United States Patent [19]

Tafesh et al.

[11] Patent Number: 5,198,585
[45] Date of Patent: Mar. 30, 1993

[54] METHOD FOR THE PREPARATION OF ARYLKETOAMINES

[75] Inventors: Ahmed M. Tafesh, Corpus Christi, Tex.; Olan S. Fruchey, Bad Soden/T.S., Fed. Rep. of Germany; Charles B. Hilton, Corpus Christi, Tex.

[73] Assignee: Hoechst Celanese Corporation, Somerville, N.J.

[21] Appl. No.: 726,063

[22] Filed: Jul. 5, 1991

[51] Int. Cl.$^5$ .................. C07C 209/52; C07C 225/10
[52] U.S. Cl. .................................... 564/343; 564/342; 564/344
[58] Field of Search ........................................ 564/343

[56] References Cited

U.S. PATENT DOCUMENTS

| | | | |
|---|---|---|---|
| 1,995,709 | 3/1935 | Hartung | 564/364 X |
| 2,505,645 | 4/1950 | McPhee | 564/365 X |
| 2,567,906 | 9/1951 | Hartung | 564/358 X |
| 2,784,228 | 3/1957 | Hartung | 564/358 |
| 3,028,429 | 4/1962 | Wilbert et al. | 564/358 |
| 3,966,813 | 6/1976 | Satzinger et al. | 564/358 |
| 5,124,489 | 6/1992 | Durrwachter et al. | 568/630 |

*Primary Examiner*—Richard L. Raymond
*Attorney, Agent, or Firm*—James J. Mullen; Donald R. Cassady; Michael W. Ferrell

[57] ABSTRACT

Acid addition salts of arylketoamines are prepared by reacting arylisonitrosoalkanones with hydrogen in the presence of a transition metal catalyst and strong acid in a dipolar aprotic solvent.

23 Claims, No Drawings

METHOD FOR THE PREPARATION OF ARYLKETOAMINES

BACKGROUND OF THE INVENTION

This invention relates to methods for the preparation of substituted or unsubstituted arylketoamines in the form of acid addition salts from substituted or unsubstituted arylisonitrosoalkanones.

Substituted and unsubstituted arylketoamines are chemical intermediates of great importance by virtue of their relationship to ephedrin and ephedrin-like substances. For example, the derivative p-hydroxyphenylethanolamine (octopamine) is a sympathomimetic which produces vasoconstricting and cardiotonic effects.

In U.S. Pat. Nos. 1,995,709 and 2,567,906 by Hartung, a multi-operations procedure for the preparation of substituted phenylpropanolamine is described, particularly, for 1-(p- or m-hydroxyphenyl)-2-amino-1-propanol (in U.S. Pat. No. 1,995,709), and 1-(p-aminophenyl)-2-amino-1-propanol (in U.S. Pat. No. 2,507,906). In U.S. Pat. No. 1,995,709, p- or m-hydroxypropiophenone is reacted with a lower alkyl nitrite in ether in the presence of hydrogen chloride to produce p- or m-hydroxyisonitrosopropiophenone, which then is separated from the reaction mixture by alkaline extraction and recovered from the alkaline solution by precipitation induced by acidification of the extract, after which the precipitate is recrystallized. The p- or m-hydroxyisonitrosopropiophenone thus separated is then reacted with hydrogen in the presence of palladium on charcoal in absolute alcohol containing dry hydrogen chloride until reduction stops, after which the amino ketone is recovered as a filtrate. The filtrate is dried and purified by recrystallization. Then the amino ketone is dissolved in water and reacted with hydrogen in the presence of palladium on charcoal. The reaction product is recovered as the hydrochloride of the amino alcohol, for example, the hydrochloride of 1-(p-hydroxyphenyl)-2-aminopropanol (in U.S. Pat. No. 1,995,709) and the hydrochloride of 1-(p-aminophenyl)-2-aminopropanol (in U.S. Pat. No. 2,507,906).

In U.S. Pat. No. 2,505,645 by McPhee, the acidic catalytic hydrogenation process described by Hartung is employed in a method of preparing α-phenyl-β-hydroxyphenyl-β-hydroxyethylamine.

U.S. Pat. No. 2,784,228 by Hartung describes an also partially aqueous alternative process for the catalytic reduction of α-oximino ketones, using alkaline solutions instead of acidic solutions to obtain a desired amino alcohol. Difficulties and shortcomings of the acidic catalytic reduction process described by hartung in U.S. Pat. Nos. 1,995,709 and 2,567,906 are detailed by Hartung in U.S. Pat. No. 2,784,228 and also by Wilbert et al. in U.S. Pat. No. 3,028,429. In U.S. Pat. No. 3,028,429, Wilbert et al. describe a process for the hydrogenation of isonitrosopropiophenone to produce 1-phenyl-2-aminopropanol which is a modification said to improve yields respecting the general process described by Hartung in U.S. Pat. Nos. 1,995,709 and 2,567,906.

U.S. Pat. No. 3,966,813 by Satzinger et al. claims a process for preparation of 1-(hydroxyphenyl)-2-aminoethanol (octopamine) by reacting a hydroxyacetophenone with a lower alkyl nitrite in a dipolar aprotic solvent in the presence of a hydrogen chloride catalyst to form isonitrosoacetophenone, and then catalytically hydrogenating the isonitrosoacetophenone in the presence of palladium to reduce the isonitroso and keto moieties on the isonitrosoacetophenone molecule. Satzinger, et al. provide several examples for the preparation of both m-hydroxyisonitrosoacetophenone and p-hydroxyisonitrosoacetophenone. However, only one example (Example 4) describes the hydrogenation step for conversion of an hydroxyisonitrosoacetophenone to a 1-(hydroxyphenyl)-2-aminoethanol. Example 4 pertains to hydrogenation of the meta substituted m-hydroxyisonitrosoacetophenone. On the basis of Example 4, Satzinger, et al. propose and claim that the para substituted p-hydroxyisonitrosoacetophenone can also be converted by the same hydrogenation step to the aminoethanol.

However, it has been discovered in the laboratories of the assignee of this invention that hydrogenation of the p-hydroxyisonitrosoacetophenone does not produce the proposed aminoethanol; instead, p-hydroxyphenethylamine (tyramine) is produced. The controlling feature appears to be the fact that the presence of a hydroxyl group at the ortho and/or para position strongly activates the benzylic carbon toward hydrogenolysis, but the presence of a hydroxyl group at the meta position on the hydroxyisonitrosoacetophenone is unable to activate the benzylic carbon toward hydrogenolysis. The unactivated benzylic carbon affects the hydrogenation reaction so that an aminoethanol is formed. The strongly activated benzylic carbon affects the hydrogenation reaction so that an ethylamine is formed. Since both para substitution and ortho substitution strongly activate the benzylic carbon, the ethylamine is formed when a hydroxyl group is present at either or both of these substitution positions.

SUMMARY OF THE INVENTION

An object of this invention is the preparation of arylketoamines in the form of their acid addition salts from unsubstituted or ortho or para position substituted arylalkanones in a one solvent process.

An object of this invention is the preparation of arylketoamines in the form of their acid addition salts from unsubstituted or ortho or para position substituted arylalkanones without use of an anhydrous alcohol.

An object of this invention is the preparation of arylketoamines in the form of their acid addition salts from unsubstituted or ortho or para position substituted arylalkanones without use of an anhydrous alcohol.

An object of this invention is the use of arylisonitrosoalkanones wherein the aryl group is unsubstituted or is substituted in the ortho and/or para position, to prepare arylketoamines in the form of their acid addition salts, in a hydrogenation method employing a transition metal catalyst without use of an anhydrous alcohol.

An object of this invention is the use of arylisonitrosoalkanones wherein the aryl group is unsubstituted or is substituted in the ortho and/or para position, to prepare arylketoamines in the form of their acid addition salts, in a hydrogenation method employing a transition metal catalyst without use of an anhydrous alcohol, wherein the hydrogenation can be conducted without controlling the amount of hydrogen introduced to the reaction mixture.

In accordance with the present invention, a method for the preparation of an arylketoamine in the form of its acid addition salts is disclosed, the method comprising the steps of:

a) providing an arylisonitrosoalkanone compound of the formula:

   (I)

wherein $R_1$ = an hydroxyl or $C_1$-$C_8$ alkyloxy radical,
$R_2$ = hydrogen or a $C_1$-$C_8$ alkyl or cycloalkyl radical, and
Ar = an unsubstituted phenyl radical, or a phenyl radical substituted at the ortho and/or para position; or a naphthyl radical unsubstituted, or substituted at one or more of the 1, 3, 6, and 7 positions; wherein one or more substituents are selected from the group consisting of hydroxyl, alkoxy, alkyl, phenyl, and benzyl radicals, wherein the alkyl component is a branched or unbranched $C_1$-$C_8$ alkyl radical, wherein any alkyl, phenyl and benzyl radicals are optionally substituted with one or more substituents selected from hydroxyl, sulfonic acid, and sulfonic acid radicals, and wherein said phenyl and benzyl substituents are optionally substituted with a $C_1$-$C_8$ alkyl or $C_1$-$C_8$ alkoxy radical, or both; and b) reacting said isonitrosoalkanone compound with hydrogen in a reaction medium comprising a dipolar aprotic solvent in the presence of transition metal catalyst and a strong acid to produce a reaction product comprising, as its major component, the acid addition salt of an arylketoamine.

In the method of this invention hydrogen is provided in sufficient quantity for reaction of 2 mole equivalents of hydrogen in the conversion of the arylisonitrosoalkanoes to an arylketoamine. Thus, stoichiometrically, the reaction may be depicted as

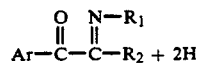

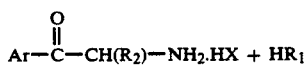

(II)

where Ar, $R_1$, and $R_2$ have the same meaning as above and X indicates the anion of a strong acid without signifying valence. Preferably the hydrogenation is conducted in the presence of hydrochloric acid to form the hydrochloride salt of the arylketoamine. When the dipolar aprotic solvent medium is used in dry condition free of water, as preferred, the hydrogenation of the arylisonitrosoalkanone compound of formula I is selective and stops after 2 mole equivalents of hydrogen per mole of the arylisonitrosoalkanone compound are consumed. Under this condition, it is not necessary to control the amount of hydrogen introduced to the reaction mixture.

The transition metal catalyst is supported on an inert support, and suitably is provided in an amount of from about 0.005% to about 1.5% by weight based on the amount of the arylisonitrosoalkanones compound. The transition metal is selected from the group consisting of platinum, palladium, nickel, rhodium, and combinations thereof, and preferably is palladium on a carbon support. The reaction is carried out under hydrogen pressure ranging from about 15 psig to about 300 psig, at temperatures ranging from 5° C. to about 100° C.

In accordance with this invention, arylketoamines in the form of their acid addition salts can be prepared from arylalkanones which are unsubstituted or substituted in the ortho or para position, using only one type solvent without having to isolate an intermediate compound.

These arylalkanones have the formula:

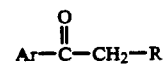   (III)

in which R represents hydrogen or a $C_1$-$C_8$ alkyl or cycloalkyl and Ar represents an aromatic phenyl radical unsubstituted, or substituted at the ortho and/or para position, or naphthyl radical unsubstituted or substituted at one or more of the 1, 3, 6, and 7 positions, wherein the substituents, one or more, are selected from the group of hydroxyl, alkoxy, alkyl, phenyl, benzyl, and aryloxy radicals, wherein the alkyl in the alkyl-containing substituent(s) is a branched or unbranched $C_1$-$C_8$ alkyl radical and any such alkyl radical as well as the phenyl and benzyl radicals may be optionally substituted with one or more substituents selected from hydroxyl, sulfonic acid, and sulfinic acid radicals, the phenyl and benzyl substituents also or alternatively being optionally substituted with one or more $C_1$-$C_8$ alkyl or $C_1$-$C_8$ alkoxy, or both, radicals. The arylalkanone of the above formula is reacted with a lower alkyl nitrite in the presence of hydrogen chloride and in a dipolar aprotic solvent to produce a reaction mixture which includes an arylisonitrosoalkanone reaction product. The reaction mixture is dried, and the dried reaction mixture is then treated with hydrogen in the presence of a transition metal catalyst as described above, and, also in the presence of a strong acid, preferably hydrogen chloride.

The drying step preferably is evaporation conducted by vacuum distillation, but solid drying agents which are adsorbents or absorbents for water may be employed to remove water, suitable adsorbents including alumina or silica gel and suitable absorbents including anhydrous sodium sulfate, calcium sulfate, magnesium sulfate, calcium carbonate, sodium hydrophosphate or the like, may be used, to remove water. Vacuum distillation preferably is conducted to also remove volatile nitrogen containing compounds, including any free amines. If water is not removed, the ensuing hydrogenation operation over-hydrogenates the arylisonitrosoalkanone intermediate produced by reacting the alkylnitrite and the arylalkanone, and side products including arylalkanolamines and arylalkylamines can result, with reduction of yield in the arylketoamine. If volatile nitrogen containing compounds having free electrons, such as amines, are present and not removed, the catalyst can be poisoned, limiting the useful life of the catalyst and reducing reaction rates or yield. When the dipolar aprotic solvent medium is dry, selective hydrogenation of the arylisonitrosoalkanone intermediate is assured and the ensuing hydrogenation reaction stops after two mole equivalents of hydrogen are consumed per mole of arylisonitrosoalkanone intermediate.

DETAILED DESCRIPTION OF THE INVENTION

In accordance with this invention, good yields of substituted and unsubstituted arylketoamines in the form of their acid addition salts are obtained by hydrogenating arylisonitrosoalkanones, wherein the aryl group is unsubstituted or is substituted at the ortho and/or para position, in the presence of a supported transition metal catalyst in a reaction medium comprising a dipolar aprotic solvent and a strong acid. The dipolar aprotic solvents employed are solvents which have a high dielectric constant and a high dipole moment but no acid hydrogen atoms; for example, such solvents include dimethylsulfoxide (DMSO), acetonitrile, dimethylformamide (DMF), dimethylacetamide and hexamethylphosphoric acid triamide (HMPT).

The substituted and unsubstituted arylisonitrosoalkanones employed in the invention have the formula:

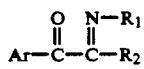

in which $R_1$ represents a hydroxyl or $C_1$-$C_8$ alkyloxy radical and $R_2$ represents hydrogen or a $C_1$-$C_8$ alkyl or cycloalkyl radical, and Ar represents an aromatic phenyl radical unsubstituted, or substituted at the ortho and/or para position, or naphthyl radical unsubstituted or substituted at one or more of the 1, 3, 6, and 7 positions, with one or more substituents selected from the group consisting of hydroxyl, alkoxy, alkyl, phenyl, benzyl, and aryloxy radicals, wherein the alkyl in the alkyl-containing substituent(s) is a branched or unbranched $C_1$-$C_8$ alkyl radical and any of such alkyl and the phenyl and benzyl radicals may be optionally substituted with one or more substituents selected from hydroxyl, sulfonic acid, and sulfinic acid radicals, the phenyl and benzyl substituents also or alternatively being optionally substituted with one or more $C_1$-$C_8$ alkyl or $C_1$-$C_8$ alkoxy, or both, radicals.

Hydrogenation of the substituted or unsubstituted arylisonitrosoalkanones is carried out using hydrogen in the presence of a transition metal hydrogenation catalyst selected from the group consisting of platinum, palladium, nickel, and rhodium or mixtures thereof on an inert support. The inert support typically comprises carbon or barium sulfate, and the hydrogenation catalyst comprises from about 1% by weight to about 25% by weight of the combination including hydrogenation catalyst and inert support. The preferred inert support material is carbon, and the most preferred hydrogenation catalyst comprises palladium on carbon, wherein the palladium comprises from about 5% by weight to about 25% by weight of the combination of palladium on carbon, as previously disclosed.

The hydrogenation is conducted under positive hydrogen pressures of from about 15 to about 300 psig, preferably in the range from about 30 to about 100 psig at temperatures suitably in the range from about 5° C. to about 100° C., preferably in the range from about 10° C. to about 50° C. At temperatures in the upper part of the useful range, the arylisonitrosalkanone conversion to the arylketoamine proceeds very rapidly and, generally speaking, better reaction control is realized in the preferred temperature range.

The strong acid, preferably hydrochloric acid, comprises from about 5% by weight to about 50% by weight of the reaction medium, and more preferably from about 10% by weight to about 20% by weight of the reaction medium.

Typically the conversion of the arylisonitrosoalkanones of the formula disclosed above to the acid addition salt of an arylketoamine, using the method of the present invention, results in a yield ranging from about 40% to about 95% based on the arylisonitrosoalkanone.

More particularly, the substituted and unsubstituted arylketoamines are obtained by reacting about two molar equivalents of hydrogen, based on the quantity of arylisonitrosoalkanone, wherein the arylisonitrosoalkanone is present in a quantity ranging from about 5% by weight to about 50% by weight, preferably from about 5% by weight to about 30% by weight, of the reaction medium, and wherein the reaction is carried out in the presence of a transition metal on an inert substrate (typically carbon), wherein the overall catalyst composition comprises from about 5% by weight to about 25% by weight, preferably from about 5% by weight to 10% by weight of the transition metal, and wherein the catalyst is present in quantity sufficient to provide from about 0.005% by weight to about 5.0% by weight, preferably from about 0.001% by weight to about 1.5% by weight, of the transition metal based on weight of the arylisonitrosoalkanone. (The reaction medium excludes the arylisonitrosoalkanone, but includes the transition metal catalyst and the solvent.)

In preferred embodiments, 1-(o- or p-hydroxyphenyl)-2-aminoethanone, i.e., α-amino-o- or p-hydroxyacetophenone, in the form of its hydrochloride salt is produced by the method of the present invention using o- or p-hydroxyisonitrosoacetophenone as the arylisonitrosoalkanones precursor. To produce 1-(o- or p-hydroxyphenyl)-2-aminoethanone, i.e., α-amino-o- or p-hydroxyacetophenone, in the form of its hydrochloride salt, the reaction medium comprises HCl in mole equivalent amount at least equal to the mole equivalent of precursor. Hydrogen is reacted in the presence of a palladium on carbon catalyst. The amount of hydrogen reacted is 2 molar equivalents based on moles of o- or p-hydroxyisonitrosoacetophenone. The hydrogen pressure in the reactor preferably ranges from about 15 psig to about 300 psig. The o- or p-hydroxyisonitrosoacetophenone is suitably present in an amount ranging from about 5% by weight to about 50% by weight of the reaction medium, preferably in an amount ranging from about 5% by weight to about 25% by weight of the reaction medium (the reaction medium excludes the o- or p-hydroxyisonitrosoacetophenone, but includes the palladium on carbon catalyst). Hydrochloric acid is suitably present in the reaction medium in an amount ranging from about 5% by weight to about 50% by weight of the reaction medium, preferably from about 10% by weight to about 20% by weight of the reaction medium. The palladium on carbon catalyst, which typically comprises about 5% by weight to about 10% by weight palladium, is present in an amount such that the palladium present ranges from about 0.005% by weight to about 1.5% by weight of the o- or p-hydroxyisonitrosoacetophenone. The arylketoamine of this invention, and most particularly the 1-(o- or p-hydroxyphenyl)-2-aminoethanone (α-amino-o- or p-hydroxyacetophenone) produced in accordance with this invention is the acid addition salt of the corresponding arylketoamine, and in the particular aspect, is the hydrochloride salt of 1-(o- or p-hydroxyphenyl)-2-aminoethanone.

In the aspect of this invention in which arylketoamines are prepared from arylalkanones using only one type solvent without having to isolate an intermediate compound, the arylalkanone has the formula:

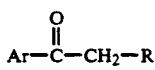

(III)

in which R represents hydrogen or a $C_1$-$C_8$ alkyl or cycloalkyl and Ar represents an aromatic phenyl radical unsubstituted, or substituted at the ortho and/or para position, or naphthyl radical unsubstituted or substituted at one or more of the 1, 3, 6, and 7 positions, wherein the substituents, one or more, are selected from the group of hydroxyl, alkoxy, alkyl, phenyl, benzyl, and aryloxy radicals, wherein the alkyl in the alkyl-containing substituent(s) is a branched or unbranched $C_1$-$C_8$ alkyl radical and any such alkyl radical as well as the phenyl and benzyl radicals may be optionally substituted with one or more substituents selected from hydroxyl, sulfonic acid, and sulfinic acid radicals, the phenyl and benzyl substituents also or alternatively being optionally substituted with one or more $C_1$-$C_8$ alkyl or $C_1$-$C_8$ alkoxy, or both, radicals.

The arylalkanone of the above formula is reacted with a lower alkyl nitrite in the presence of hydrogen chloride and in a dipolar aprotic solvent to produce a reaction mixture which includes an arylisonitrosoalkanone reaction product. The reaction mixture is then treated to remove water inclusive of water of reaction from the reaction mixture, suitably by evaporation—preferably at reduced pressures (vacuum distillation), most preferably at reduced pressures at which any volatile catalyst poisons present, such as amines, are also removed—or by contacting the reaction mixture with a drying agent which is an adsorbent or absorbent for the water. Vacuum distillation is preferred for industrial applications. Drying agents are suitable for small batch operations.

Vacuum distillation suitably is conducted at negative (relative to atmospheric) pressures of from 0.2 mmHg to 20 mmHg at temperatures within the range from 30° to 80° C., preferably at negative pressures from 0.2 to 1 mmHg and temperatures from 30° to 50° C. Suitable drying agents include solid adsorbents such as silica gel and activated alumina, which remove water by surface adsorption, and solid absorbents such as sodium sulfate, calcium sulfate, magnesium sulfate, calcium carbonate, sodium hydrophosphate and the like.

Examples of arylkanones usable in the above-described process are those wherein the aryl of the arylalkanone is an unsubstituted phenyl or naphthyl radical or is a substituted phenyl or naphthyl radical having substitution of the kind previously described. Such arylalanones include, but are not limited to, o-and p-hydroxyacetophenone, o-, and p-methylacetophenone, p-ethylacetophenone, p-propylacetophenone, p-butylacetophenone, o- and p-methoxyacetophenone, o-and p-ethoxyacetophenone, 2,4-methoxyacetophenone, p-phenylacetophenone, 2-methoxy-4-methylacetophenone, α-acetonaphthone, β-acetonapthone, propiophenone, o- and p-methoxypropiophenone, p-methylpropiophenone, p-ethylpropiophenone, butyrophenone, p-methylbutyrophenone, p-methoxybutyrophenone, valerophenone and p-methylvalerophenone, p-acetamidopropiophenone, p-hydroxyphenylacetophenone, p-hydroxyphenylpropiophenone, 1-(4-methylphenyl)propiophenone, and p-phenylsulfonyl-acetophenone, 4,5 dihydroxy-1-indanone, 5,6-dihydroxy-1-indanone, 4,5 dimethoxy-1-indanone and 5,6-dimethoxy-1-indanone.

An arylalkanone of the above and foregoing formula is reacted with a lower alkylnitrite in the presence of hydrogen chloride in a dipolar aprotic solvent.

The dipolar aprotic solvents employed are solvents which have a high dielectric constant and a high dipole moment but no acid hydrogen atoms; for example, such solvents include dimethylsulfoxide (DMSO), acetonitrile, dimethylformamide (DMF), dimethylacetamide and hexamethylphosphoric acid triamide (HMPT). Suitable alkyl nitrites are lower alkyl nitrites in which the alkyl radical has from 1 to 8 carbon atoms; for example, methylnitrite, ethylnitrite, isopropylnitrite, n-butylnitrite, t-butylnitrite, amylnitrite, n-hexylnitrite, n-heptylnitrite, n-octylnitrite and the like.

The reaction of the arylalkanone with the lower alkyl nitrite suitably can be carried out at a temperature in the range from −30° C. to 100° C., preferably in the range from 10° C. to 50° C. The amount of hydrogen chloride used suitably is from about 0.5 to 5.0 equivalents, relative to the arylalkanone used. Respecting suitable dipolar aprotic solvents and lower alkyl nitrites and conditions for this aspect of the invention, reference is made to U.S. Pat. No. 3,966,813.

The following examples illustrate the invention, and are not to be understood as limiting the invention only to these embodiments.

EXAMPLE I

To a three-neck 2 L flask is added 2.2 moles of dry HCl to 1000 mL of dry dimethyl formamide (DMF). To the flask is then added 272 grams (2 moles) of p-hydroxyacetophenone all at once. The mixture is stirred until all solid dissolved. Then, 296 mL (2.2 moles) of 90% tertiary butyl nitrite (in tertiary butanol) is added very slowly to maintain the reaction medium temperature at about 40° C., which takes about two hours, after which the reaction medium is stirred for an additional three hours while maintaining the temperature at about 40°-45° C., and the reaction was left overnight at room temperature. A 200 mL sample is taken from the reaction mixture and was subjected to high vacuum (30° C., 28 inches water) whereupon water in the sample is evaporated and the reaction mixture is dry.

After filtration the crude but dry hydroxyisonitrosoacetophenone solution is added to a 1 L autoclave reactor, which is pressure checked, is charged with 12.5 g of 5% palladium on carbon and 178 mL of 4.2M HCl in dry DMF. The reactor is sealed then degassed three times with nitrogen and three times with hydrogen. The reactor is then pressurized to 100 psi with hydrogen and stirred at 1200 rpm. The reaction heated itself to 27.6° C. The course of the reaction is tabularized.

| Time | Temperature (°C.) | Reactor Pressure (psig) | Surge Vessel Pressure (psig) |
|---|---|---|---|
| 11:00 | 25.5 | 102 | 436 |
| 11:30 | 26.8 | 102 | 434 |
| 12:30 | 27.6 | 102 | 420 |
| 13:40 | 27.4 | 102 | 406 |
| 14:05 | 27.6 | 98 | 403 |
| 15:00 | 26.6 | 98 | 320 |
| 15:20 | 26.7 | 98 | 386 |
| 16:00 | 27.2 | 98 | 382 |
| 21:00 | 26.2 | 98 | 315 |

The reaction mixture from the reactor is filtered and then concentrated under reduced pressure and the crude brown crystals are recrystallized from ethanol to give, after drying pure α-amino-p-hydroxyacetophenone in 70% yield.

The above and foregoing examples are illustrative only, and many variations can be made without departing from the spirit and scope of the present invention as encompassed by the following claims.

What is claimed is:

1. A method of preparing an acid addition salt of an arylketoamine, which comprises:
   a) providing a compound of the formula

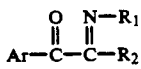

wherein,
$R_1$ = an hydroxyl or $C_1$-$C_8$ alkyloxy radical,
$R_2$ = hydrogen or a $C_1$-$C_8$ alkyl or cycloalkyl radical, and
Ar = an unsubstituted phenyl radical, or a phenyl radical substituted at the ortho position, the para position, or both the ortho and para positions, or an unsubstituted naphthyl radical, or a naphthyl radical substituted at one or more of the 1, 3, 6, and 7 positions, wherein the substituents are selected from the group consisting of hydroxyl, alkoxy, alkyl, phenyl, and benzyl radicals, wherein the alkyl component is a branched or unbranched $C_1$-$C_8$ alkyl radical, wherein any of said alkyl, phenyl, and benzyl radicals are optionally substituted with one or more substituents selected from hydroxyl, sulfonic acid, and sulfinic acid radicals, and wherein said phenyl and benzyl substituents are optionally substituted with a $C_1$-$C_8$ alkyl or $C_1$-$C_8$ alkoxy radical, or both; and
   b) reacting said compound with hydrogen in a reaction medium comprising a dipolar aprotic solvent and a strong acid and a hydrogenation catalyst comprising a transition metal catalyst on an inert support, to produce a reaction product comprising an arylketoamine as a major compound.

2. The method of claim 1 in which said solvent is selected from dimethylsulfoxide, acetonitrile, dimethylformamide, diethylacetamide and hexamethylphosphoric acid triamide.

3. The method of claim 1 in which said strong acid is hydrochloric acid present in an amount of from about 5 to about 50 weight percent of the formula of step a).

4. The method of claim 1, in which the amount of hydrogen reacted in step b) is 2 molar equivalents, based on the moles of the compound of said formula of step a).

5. The method of claim 4, wherein the reaction is carried out under hydrogen pressure ranging from about 15 psig to about 300 psig, at temperatures ranging from about 5° C. to about 100° C.

6. A method of producing the hydrochloride salt of α-amino o- or p-hydroxyacetophenone, which comprises the steps of:
   a) providing the compound o- or p-hydroxy-α-isonitrosoacetophenone;
   b) reacting said compound with hydrogen in a reaction medium comprising a dipolar aprotic solvent, hydrochloric acid, and a transition metal catalyst on an inert support.

7. The method of claim 6, wherein said hydrochloric acid is present in an amount of from about 5 to about 50 weight percent.

8. The method of claim 7, wherein in step b) two moles of hydrogen are reacted per mole of said compound of step a).

9. The method of claim 8, wherein said transition metal is selected from the group consisting of platinum, palladium, nickel, rhodium, and combinations thereof.

10. The method of claim 9, wherein said hydrogenation catalyst is palladium.

11. The method of claim 10, wherein said palladium, excluding said inert support, is present in a quantity ranging from about 0.005% by weight to about 1.5% by weight based on the weight of said compound of step a).

12. The method of claim 11, wherein the reaction is carried out under hydrogen pressure ranging from about 15 psig to about 300 psig, at temperatures ranging from about 5° C. to about 100° C.

13. The method of claim 12, wherein the o- or p-hydroxyisonitrosoacetophenone is present initially in said reaction medium in an amount ranging from about 5% by weight to about 50% by weight, of said reaction medium, and wherein said supported palladium catalyst is present in said reaction medium at a concentration ranging from about 0.01% by weight to about 10% by weight of said reaction medium.

14. The method of claim 13, wherein said o- or p-hydroxyisonitrosoacetophenone is present initially in said reaction medium in an amount less than about 30% by weight of said reaction medium.

15. The method of preparing an acid addition salt of an arylketoamine, which comprises:
   a) providing an arylalkanone of the formula:

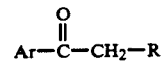

in which R represents hydrogen or a $C_1$-$C_8$ alkyl or cycloalkyl and Ar represents an aromatic phenyl radical unsubstituted, or substituted at the ortho and/or para position, or naphthyl radical unsubstituted or substituted at one or more of the 1, 3, 6, and 7 positions, wherein the substituents, one or more, are selected from the group of hydroxyl, alkoxy, alkyl, phenyl, benzyl, and aryloxy radicals, wherein the alkyl in the alkyl-containing substituent(s) is a branched or unbranched $C_1$-$C_8$ alkyl radical and any such alkyl radical as well as the phenyl and benzyl radicals may be optionally substituted with one or more substituents selected from hydroxyl, sulfonic acid, and sulfitic acid radicals, the phenyl and benzyl substituents also or alternatively being optionally substituted with one or more $C_1$-$C_8$ alkyl or $C_1$-$C_8$ alkoxy, or both, radicals,
   b) reacting said arylalkanone with a lower alkyl nitrite in the presence of a strong acid and a dipolar aprotic solvent to produce a reaction mixture which includes an arylisonitroso-alkanone reaction product and water of reaction in said solvent,
   c) removing water from said reaction mixture, and
   d) contacting said dried reaction product with hydrogen and a strong acid in a dipolar aprotic solvent in the presence of a hydrogenation catalyst comprising a transition metal catalyst on an inert support.

16. The method of claim 1 or 15, wherein the amount of said transition metal present ranges from about 0.005% by weight to about 1.5% by weight of said compound of step a).

17. A method of claim 16, wherein said transition metal is selected from the group consisting of platinum, palladium, nickel, rhodium, and combinations thereof.

18. The method of claim 15, wherein said step (c) comprises evaporating said water of reaction.

19. The method of claim 15, wherein said step (c) comprises contacting said reaction mixture with a drying agent for absorbing said water of reaction.

20. The method of claim 15, wherein said step (c) comprises contacting said reaction mixture with a solid adsorbent for adsorbing said water of reaction.

21. The reaction of claim 15 in which said arylalkanone is o- or p-hydroxyacetophenone, said strong acid in steps (b) and (c) is hydrochloric acid, and said hydrogenation catalyst is palladium on a carbon support.

22. The method of claim 21 in which said solvent of steps (b) and (d) is selected from dimethylsulfoxide, acetonitrile, dimethylformamide, diethylacetamide and hexamethylphosphoric acid triamide.

23. The method of claim 22 in which said palladium, exclusive of said carbon support, is present in a quantity ranging from about 0.005% by weight to about 1.5% by weight based on the weight of said o- or p-hydroxyacetophenone, and wherein said step (d) reaction is conducted under hydrogen pressure ranging from about 15 psig to about 300 psig at temperatures in the range of from about 5° C. to about 100° C.

* * * * *

UNITED STATES PATENT AND TRADEMARK OFFICE
CERTIFICATE OF CORRECTION

PATENT NO. : 5,198,585

DATED : March 30, 1993

INVENTOR(S) : Ahmed M. Tafesh, et al

It is certified that error appears in the above-indentified patent and that said Letters Patent is hereby corrected as shown below:

On the title page, item [75], Werner H. Mueller should be added as an inventor.

Signed and Sealed this

Twentieth Day of December, 1994

Attest:

BRUCE LEHMAN

Attesting Officer     Commissioner of Patents and Trademarks